United States Patent [19]
Bryant

[11] Patent Number: 6,019,976
[45] Date of Patent: Feb. 1, 2000

[54] FORMULATIONS FOR TREATING MALE PATTERN BALDNESS CONTAINING SERENOA REPENS, VITAMIN B6, VITAMIN B3, ZINC AND L-ARGININE

[76] Inventor: Andrew Edward Bryant, Little Trewollack, St. Wenn, Bodmin, Cornwall PL30 5PL, United Kingdom

[21] Appl. No.: 09/047,644

[22] Filed: Mar. 25, 1998

[51] Int. Cl.⁷ .......................... A61K 35/78; A61K 33/30; A61K 31/195; A61K 31/44
[52] U.S. Cl. ..................... 424/195.1; 424/641; 424/642; 426/656; 514/880; 514/904; 514/905
[58] Field of Search ................................. 424/195.1, 641, 424/642; 426/656; 514/880, 904, 905

[56] References Cited

U.S. PATENT DOCUMENTS 5,543,146  8/1996  Perez .

FOREIGN PATENT DOCUMENTS

| 0287000 A1 | 4/1988 | European Pat. Off. . |
| 2223925A | 4/1990 | United Kingdom . |
| WO 94/26240 A1 | 11/1994 | WIPO . |
| 97/02041 | 1/1997 | WIPO . |
| WO 97/02041 A1 | 1/1997 | WIPO . |

*Primary Examiner*—David M. Naff
*Assistant Examiner*—Janet M. Kerr
*Attorney, Agent, or Firm*—Melvin I. Stoltz

[57] ABSTRACT

The invention relates to therapeutic formulations containing 75 to 85% by weight of a *serenoa repens* extract, 2 to 5% by weight of vitamin B6, 2 to 5% by weight of vitamin B3, 2 to 5% by weight of zinc salt, and 10 to 15% by weight of L-arginine. The therapeutic formulations can be used to treat male pattern baldness by topical application to the hair.

3 Claims, No Drawings

FORMULATIONS FOR TREATING MALE PATTERN BALDNESS CONTAINING SERENOA REPENS, VITAMIN B6, VITAMIN B3, ZINC AND L-ARGININE

FIELD OF THE INVENTION

This invention relates to therapeutic formulations and to the preparation and administering of such formulations.

The invention has been developed initially in relation to the combating or alleviation of male pattern baldness, but is believed to have wider applications.

The formulation includes an extract obtained from the fruits of the Saw Palmetto, also known as *Serenoa repens*. One method of obtaining this extract is described in French Patent Specification No. 2 480 754 and involves the use of a polar solvents in the presence of anti-oxidants and in an inert atmosphere. Another method of obtaining this extract is described in European Patent Specification No. 0 250 953 and involves the use of carbon dioxide as the solvent under high pressure conditions, for example, at pressures ranging from 100 to 350 bars and at temperatures ranging from 30° C. to 50° C.

It is believed that extracts obtained from the fruits or berries of other members of the Palmaae family will have properties similar to those obtained from the Saw Palmetto or *Serenoa repens*. When, therefore, reference is made below to the use of *Serenoa repens* extract, such reference is to be interpreted, where appropriate, as including reference to extracts obtained from the fruits or berries of other members of the Palmaae family.

It is an object of the present invention to provide an improved therapeutic formulation and, in particular, to provide a formulation which provides enhanced activity in combating male pattern baldness.

It is known that DHT inhibitors, i.e. substances which inhibit the production of dihydrotestosterone, have been used orally to stop excessive hair loss and, in some instances, have reversed hair loss in traditional male pattern baldness. Tests have, however, indicated that the oral use of the known DHT inhibitors can produce male impotence in a small percentage of users, i.e. about 1 to 2% of the users have become impotent.

It is accordingly an object of the present invention to provide a therapeutic formulation and a method of administration such as to avoid these undesirable side effects.

SUMMARY OF THE INVENTION

According to a first aspect of the present invention there is provided a therapeutic formulation which includes *Serenoa repens* extract together with at least one mineral and at least one vitamin.

The formulation preferably includes more than one mineral and more than one vitamin. Preferred minerals include zinc, copper, magnesium and manganese salts. Preferred vitamins include Vitamin B6, Vitamin C and biotin.

The formulation preferably also includes at least one amino-acid. The preferred amino-acid is L-Arginine.

According to a second aspect of the present invention there is provided a method of preparing a formulation for use in combating male pattern baldness which includes mixing *Serenoa repens* extract with at least one mineral and at least one vitamin.

Increased hair loss has been associated with an increased likelihood to suffer from coronary heart disease. Coronary heart disease is the main cause of adult deaths in the United States and it is accordingly a further object of the present invention to provide a method of preparing a formulation for use in reducing the incidence of coronary heart disease.

According to this aspect of the present invention there is provided a method of preparing a formulation for use in reducing the incidence of coronary heart disease, which method includes mixing *Serenoa repens* extract with at least one soya isolate, at least one mineral and at least one vitamin.

The invention thus further provides a nutritional supplement which includes *Serenoa repens* extract, at least one soya isolate, at least one mineral and at least one vitamin.

The formulation may also include at least one amino-acid, the preferred amino-acid being L-Arginine.

The nutritional supplement may be in the form of a powder which can be added to, for example, water, milk or fruit juices to form a nutritional and therapeutic drink.

In one example of the present invention, a base for a nutritional supplement is prepared by mixing together the following ingredients:

a) soya isolates,
b) stone-ground brown rice flour,
c) dried whole apples (for flavour),
d) Psyllium husks (fibre),
e) vitamins,
f) minerals,
g) vanilla (flavouring),
h) Royal jelly (3×concentrate), and
i) Aloe Vera powder (200×concentrate).

To this base material, the following further ingredients are added at the amounts indicated per 10 gms. of the above base material:

1) *Serenoa repens* extract—750 mgms.,
2) zinc—20 mgms.,
3) magnesium—180 mgms.,
4) manganese—100 mgms.,
5) Vitamin B6—15 mgms., and
6) L-Arginine—150–200 mgms.

The zinc is preferably added in the form of one or more zinc salts, for example, zinc sulphate, zinc ascorbate and zinc methionine. The magnesium and manganese are also added in the form of one or more magnesium and manganese salts, The supplement is then added to water, milk or fruit juice to form a drink and a typical dosage will be of 40 gms. (i.e. two standard scoops) in a suitable quantity of liquid. This may be taken up to three times a day.

The drink is a low fat energy source which has a slight laxative effect. The laxative effect is of advantage in that it stops the reabsorption of hormones from the digestive tract. The drink contains no sugar and can be formulated to provide an equal balance of proteins to carbohydrates—which stops an insulin rise. Stopping a rise in the insulin level is important as insulin levels have an inverse relationship with the level of Sex Hormone Binding Globulin (SHBG). SHBG is a carrier molecule to which testosterone attaches and is transported through the blood. Free testosterone (i.e. that which is not attached to SHBG) can convert to dihydrotestosterone (DHT) which is the hormone which causes hair loss and prostate problems. It will thus be seen that a rise in insulin levels can result indirectly in a rise in the level of DHT. Avoiding an insulin rise is accordingly important.

The inclusion of soya isolates is of advantage in that soya contains three amino acids, i.e. glutamic acid, alanine and glycine, which have been shown to be beneficial in reducing prostate problems.

The nutritional supplement is preferably supplied in combination with a questionnaire to be completed by the person taking the supplement and providing a record of the effects of taking the supplement. Typical questions for a person taking the supplement to reduce hair loss might be as follows:

1. How many scoops of supplement have you been taking per day for the last week?
2. Have you taken them regularly since the commencement date?
3. Is the hair at your temples receding?
4. Do you have a bald spot on the crown of your head?
5. Do you now notice less hair on your pillow?
6. Have you noticed less hair in the shower trap/bath?
7. Does your hair look better?
8. Estimate your rate of hair loss before taking the supplement on a scale running from 1 to 5.
9. Estimate the current rate of hair loss on the same scale.
10. Have you noticed when shaving that your beard growth has become finer?
11. Do you have much hair on your arms?
12. Do you have much hair on your chest?
13. Have you noticed that the amount of hair on your arms and chest has been increasing?
14. How many cups or glasses of tea, coffee or alcohol do you drink per day?

For a person with prostate problems, a different questionnaire will be provided and the user will be asked to give comparative answers, i.e. comparing his present condition with that which obtained before he started taking the supplement, in the following respect:

1. Difficulty passing urine.
2. Difficulty starting urination.
3. Intermittency.
4. Terminal dribbling.
5. Sensation of not fully emptying the bladder.
6. Weak urine stream.
7. Sudden need to urinate.
8. Average day-time frequency.
9. Average night-time frequency.
10. Sex drive.

Information will also be asked for in respect of the number of cups or glasses of tea, coffee, beer, wines and spirits drunk per day. The answers to the questionnaire and the above information will be of assistance to the supplier of the supplement in monitoring its effectiveness and in assessing any increase or reduction in the daily amount of the supplement to be used per day.

As opposed to providing the supplement in the form of a powder to be made into a drink, the supplement may be in the form of capsules formed of gelatine and glycerine and containing the appropriate ingredients. The number of milligrams of the ingredients in a capsule may be as follows:

Serenoa repens extract—up to 125,
Vitamin B6—up to 15,
Zinc ascorbate—up to 60,
Zinc methionine—up to 60,
Magnesium ascorbate—up to 180,
Manganese citrate—up to 100, and
L-Arginine—up to 25.

The person taking the capsules will take from one to six capsules per day and ideally will have them spaced out during the day. The capsules will normally be in the form of soft gel capsules.

As an alternative to taking capsules containing all the appropriate ingredients, the person taking the supplement may be given two different kinds of capsules, i.e. one kind containing only the Serenoa repens extract and the other kind containing the other recommended ingredients plus a smaller amount of the Serenoa repens extract. In some cases, only the capsules containing the smaller amount of the Serenoa repens extract will be required.

As opposed to providing the supplement in capsule form, it may be in the form of a sublingual lipospray containing the appropriate ingredients as specified above, together with a vasodilator, such as Vitamin B3 and L-Arginine (an amino acid). The lipospray is based on the use of liposomes, i.e. hollow fat molecules, and the method of use, i.e. spraying under the tongue, ensures that the contents of the spray pass straight into the bloodstream bypassing the digestion and the first pass of the liver, where such substances would normally be extracted. Suitable methods for the production of liposprays are described in U.S. Pat. Nos. 4,761,288 and 4,897,269, to which reference should be made.

The user is given instructions as to the number of pumps of the spray he is to use on each occasion and he will spray the substance under his tongue and swallow the residual.

The action of the nutritional supplement is complex. In the preferred formulation described above, the zinc salts and the vitamin B6 combine to reduce the hormone prolactin. Prolactin increases production of dihydrotestosterone (DHT) and binding of the DHT to the cellular receptors. An important advantage of the formulation of the present invention is thus that it involves the use of minerals and vitamins to reduce the production of prolactin.

As a further form of application, particularly for a person suffering from hair loss, a formulation for topical application will be provided. In such case, the Serenoa repens extract which is used will be treated so that it is colourless and therefore does not cause overnight discoloration of the pillow. The basic Serenoa repens extract normally has a fatty acid content of between 85 and 95% by weight and the method of treatment of the extract for use in the topical application will normally involve the removal of the majority of the fatty acid content while leaving the active metabolites, the principal ones of which are believed to be β-sitosterol and campesterol.

The formulation for topical application may thus be in the form of a white cream comprising liposomes (hollow fat molecules) within which the following ingredients are incorporated in the proportions indicated:

a) Serenoa repens extract (treated as described above)—75 to 85% by weight,
b) vitamin B6—2 to 5% by weight,
c) zinc salt, e.g. zinc ascorbate—2 to 5% by weight,
d) vitamin B3—2 to 5% by weight, and
e) L-Arginine (an amino acid)—10 to 15% by weight.

A recommended quantity of the formulation will be applied to the hair each evening and will then be washed off in the morning.

I claim:

1. A method for preparing a therapeutic topical formulation for treating male pattern baldness comprising admixing 75 to 85% by weight Serenoa repens extract, 2 to 5% by weight vitamin B6, 2 to 5% by weight zinc salt, 2 to 5% by weight vitamin B3, and 10 to 15% by weight L-arginine to obtain said formulation.

2. A therapeutic topical formulation for treating male pattern baldness prepared by the method of claim 1.

3. A method for treating male pattern baldness comprising topically applying to the hair a physiologically effective amount of the composition of claim 2.

* * * * *